(12) United States Patent
Elsbernd et al.

(10) Patent No.: US 6,656,258 B2
(45) Date of Patent: Dec. 2, 2003

(54) COMPOSITIONS COMPRISING FLUORINATED SILANES AND COMPRESSED FLUID $CO_2$

(75) Inventors: Cheryl L. S. Elsbernd, Woodbury, MN (US); Michael S. Terrazas, Prescott, WI (US); Steven J. Martin, Shoreview, MN (US); Mark J. Pellerite, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 221 days.

(21) Appl. No.: 09/838,415

(22) Filed: Apr. 19, 2001

(65) Prior Publication Data

US 2002/0192380 A1 Dec. 19, 2002

Related U.S. Application Data

(60) Provisional application No. 60/277,410, filed on Mar. 20, 2001.

(51) Int. Cl.$^7$ .............................. C09D 7/00; C09D 5/00
(52) U.S. Cl. ............................ 106/287.1; 106/287.11; 106/287.13; 106/287.14
(58) Field of Search ...................... 106/287.1, 287.11, 106/287.13, 287.14

(56) References Cited

U.S. PATENT DOCUMENTS

| | | | |
|---|---|---|---|
| 3,574,770 A | | 4/1971 | Paine et al. |
| 3,646,085 A | | 2/1972 | Bartlett |
| 3,810,874 A | | 5/1974 | Mitsch et al. |
| 3,950,588 A | | 4/1976 | McDougal |
| 4,923,720 A | | 5/1990 | Lee et al. |
| 5,027,742 A | | 7/1991 | Lee et al. |
| 5,066,522 A | | 11/1991 | Cole et al. |
| 5,108,799 A | | 4/1992 | Hoy et al. |
| 5,211,342 A | | 5/1993 | Hoy et al. |
| 5,225,190 A | * | 7/1993 | Halloran et al. ....... 424/70.121 |
| 5,274,159 A | | 12/1993 | Pellerite et al. |
| 5,306,758 A | | 4/1994 | Pellerite |
| 5,702,509 A | * | 12/1997 | Pellerite et al. ................. 106/2 |
| 5,760,126 A | * | 6/1998 | Engle et al. ................. 524/516 |
| 5,851,674 A | | 12/1998 | Pellerite et al. |
| 5,863,612 A | | 1/1999 | DeSimone |
| 5,922,833 A | | 7/1999 | DeSimone |
| 6,030,663 A | | 2/2000 | McClain et al. |
| 6,127,000 A | | 10/2000 | Carbonell et al. |
| 6,235,701 B1 | * | 5/2001 | Senger Elsbernd ......... 510/412 |
| 6,287,640 B1 | | 9/2001 | McClain et al. |

FOREIGN PATENT DOCUMENTS

| | | |
|---|---|---|
| EP | 0 789 050 A2 | 8/1997 |
| EP | 1 006 168 A1 | 6/2000 |
| JP | 62-238867 | 10/1987 |
| WO | WO 98/40439 | 9/1998 |
| WO | WO 99/19080 | 4/1999 |
| WO | WO 99/37720 | 7/1999 |
| WO | WO 00/27544 | 5/2000 |
| WO | WO 00/56450 | 9/2000 |

OTHER PUBLICATIONS

U.S.S.N. 09/689,013, filed Oct. 12, 2000, "Compositions Comprising Fluorinated Polyether Silanes for Rendering Substrates Oil and Water Repellent", pp. 1–26.

W.C. Bunyard, F.E. Henon, S.N. Burns, R.W. Linton, R.G. Carbonell, J.M. DeSimone, "Synthesis of Novel Perfluoropolyethers for Carbon Dioxide–Based Coatings Technologies", University of North Carolina, Dept. of Chemistry, pp. 1–10, no date provided.

J. Lewis, J.N. Argyropoulos, K.A. Nielson, "Supercritical Carbon Dioxide Spray Systems", Metal Fininshing, (Apr., 1997).

Encyclopedia of Chemical Technology, 4$^{th}$ Edition, "Supercritical Fluids", N.Y., John Wiley and Sons, vol. 23, pp. 452–477.

K.A. Nielsen, J.N. Argyropoulos, D.C. Busby, D.J. Dickson, C.S. Lee, "Enhanced Performance and Improved Economics of Supercritical Fluid Applied Coatings", pp. 151–160 (Feb. 22–24, 1995) Waterborne, High–Solids, and Powder Coatings Symposium.

W.C. Bunyard, F.E. Henon, S.N. Burns, R.W. Linton, R.G. Carbonell, J.M. DeSimone, "Synthesis of Novel Perfluoropolyethers for Carbon Dioxide–Based Coatings Technologies", University of North Carolina, Dept. of Chemistry, pp. 1–10, no date provided.

J. Lewis, J.N. Argyropoulos, K.A. Nielson, "Supercritical Carbon Dioxide Spray Systems", Metal Fininshing, (Apr., 1997).

* cited by examiner

Primary Examiner—David Brunsman
(74) Attorney, Agent, or Firm—Kent S. Kokko (57) ABSTRACT

The present invention provides composition for treating a substrate comprising a homogeneous mixture of:

(a) a fluorinated silane of the formula:

$$Rf_j^1\text{-}[\text{-}Q\text{-}SiY_{3\text{-}x}R^1_x]_y \qquad (I)$$

wherein $R_f^1$ represents a monovalent or divalent perfluorinated group, Q represents an organic divalent linking group, $R^1$ represents a $C_1$–$C_4$ alkyl group, Y represents a hydrolysable group; x is 0 or 1 and y is 1 or 2;

(b) compressed fluid carbon dioxide; and (c) optionally an organic or inorganic acid.

The invention further provides a method of making such a composition and the use thereof to treat substrates to render them oil and water repellent.

16 Claims, 3 Drawing Sheets

COMPOSITIONS COMPRISING FLUORINATED SILANES AND COMPRESSED FLUID CO₂

CROSS REFERENCE TO RELATED APPLICATION

This application claims priority to U.S. Provisional Patent Application No. 60/277,410, filed Mar. 20, 2001.

FIELD OF THE INVENTION

The present invention relates to a method of treating substrates, in particular substrates having a hard surface such as ceramics, to render them water, oil, stain and dirt repellent. The present invention also relates to compositions for use in such a method.

BACKGROUND OF THE INVENTION

Fluorinated silanes, i.e. silane compounds that have one or more fluorinated groups for rendering substrates such as glass and ceramics oil and water repellent, have been long known. Commercial products are available that comprise a silane having one or more hydrolysable groups and at least one non-hydrolysable fluorinated alkyl group. The products are used to treat ceramic or glass surfaces and are generally applied in the presence of an acid catalyst such as acetic acid. Although good repellency results are obtained with such products, there continues to be a desire to further improve them, in particular the durability and the coating efficiency.

Fluorinated polyether silanes are also known in the art. For example, EP 789050 discloses the use thereof for making composite film coatings. U.S. Pat. No. 3,646,085 teaches fluorinated polyether silanes for rendering glass or metal surfaces oil and water repellent. The surfaces are rendered oil and/or water repellent by treating them with a solution of the fluorinated polyether silane in ethanol or in 1,2,2-trichloro-1,1,2-trifluoroethane. U.S. Pat. No. 5,851,674 and WO 99/37720 disclose fluorinated silanes for providing an antisoiling coating to antireflective surfaces on substrates such as glass or plastic. It is taught to apply the fluorinated silane from a solution in an aprotic solvent. The necessary amount of water for the condensation reaction is supplied by allowing the treated substrates to cure in an environment of sufficient humidity.

U.S. Pat. No. 3,950,588 discloses the use of fluorinated polyether silanes to render ceramic surfaces such as bathroom tiles or cookware water and/or oil repellent. It is taught in this document that care should be taken that the coating composition is contained in an anhydrous state prior to application. Also, it is recommended in this document that the surface to be treated be free of water as a separate phase. The necessary water for the polycondensation reaction at the surface is derived from adsorbed water in the ceramic and/or the environment.

U.S. Pat. No. 6,127,000 (DeSimone et al.) describes a method of protecting substrates by applying a composition comprising carbon dioxide and a fluoropolyether, the fluoropolyethers optionally having anchoring groups such as carboxylic acids, esters or amides, to enhance the adsorption of the fluoropolyether to the substrate.

Although many fluorinated silane compositions are known in the art for treating substrates to render them oil and water repellent, there continues to be a desire to provide further compositions for the treatment of substrates, in particular substrates having a hard surface such as ceramics, in order to render them water and oil repellent. Desirably, such compositions and methods employing them can yield coatings that have improved properties. In particular, it would be desirable to improve the durability of the coating, including an improved abrasion resistance of the coating. The compositions can preferably be applied in an easy, convenient, and safe way and are compatible with existing manufacturing methods. Preferably, the compositions will fit easily in the manufacturing processes that are practiced to produce the substrates to be treated. The compositions preferably also avoid or minimize the use of volatile organic compounds while making efficient use of the fluorinated silane.

SUMMARY OF THE INVENTION

The present invention provides in one aspect a composition for treating a substrate comprising a homogeneous mixture of
(a) at least one fluorinated silane of the formula:

$$R_f^1\text{-}[\text{-}Q\text{-}SiY_{3-x}R^1{}_x]_y \qquad (I)$$

wherein $R_f^1$ represents a monovalent or divalent perfluorinated group, optionally containing one or more ether oxygen atoms; Q represents an organic divalent linking group, $R^1$ represents a $C_1$–$C_4$ alkyl group, Y represents a hydrolysable group; x is 0 or 1 and y is 1 or 2;
(b) compressed fluid carbon dioxide; and
(c) optionally an organic or inorganic acid.

It has been found that when a fluorinated silane of formula (I) is applied from a mixture that includes compressed fluid carbon dioxide, extremely thin oil- and water-repellent coatings can be provided, with efficient use of the fluorinated silane. Furthermore, the compositions spread well on the substrate to be treated with the result that uniform properties can be achieved over the whole surface of the treated substrate. Still further, the composition minimizes or eliminates the use of volatile organic compounds (VOCs), thereby reducing pollution and exposure to potentially harmful, and often flammable, solvent vapors.

As used herein the term "compressed fluid", with reference to carbon dioxide, means a supercritical fluid, a near-critical fluid, an expanded liquid or a highly compressed gas, depending on the temperature, pressure and composition. See, for example, *Supercritical Fluids*, Encyclopedia of Chemical Technology, 4$^{th}$ Edition, John Wiley and Sons, N.Y, vol. 23, pp. 453.

The compressed fluid carbon dioxide may be present in the supercritical, compressed gas, near-critical fluid, expanded liquid or liquid states and may be used to prepare the compositions of this invention. If liquid $CO_2$ is used in the compositions or processes of this invention, the temperature is generally below about 31° C. If compressed gaseous $CO_2$ is used, the pressure is generally from about 20 to 75 bar (2 to 7.6 MPa). The $CO_2$ may also be used in the supercritical state, i.e. at or above that temperature (31° C.) at which $CO_2$ cannot be liquefied by further increases in pressure. The thermodynamic properties of $CO_2$ are described, for example, in McHugh and Krukonis, *Supercritical Fluid Extraction*, Butterworth-Heinemann, N.Y., 1994. The physical state of compressed fluid $CO_2$ depends on the operating temperatures and pressures at which the desired end use is typically accomplished.

By the term 'homogeneous mixture' in connection with the present invention is meant that the composition is stable, i.e. no precipitation or phase separation occurs, for at least the amount of time necessary to prepare the composition and to apply it to the substrate. Generally, this means that the composition should be stable for at least one hour. The compositions suitable for use in this invention may be clear solutions as well as somewhat hazy mixtures.

Although the compositions may be prepared by combining the fluorinated silane directly with the compressed fluid carbon dioxide, it may be more convenient to prepare the compositions of the invention by diluting a concentrate comprising the fluorinated silane of formula (I). Accordingly, in a further aspect, the invention provides a method for making a composition for the treatment of a substrate, the method comprising combining a solution of a fluorinated silane of formula (I) in an organic solvent and compressed fluid carbon dioxide, and optionally an organic or inorganic acid, so as to prepare a homogeneous mixture containing between 0.01 and 5% by weight of the fluorinated silane in compressed fluid carbon dioxide. The organic solvent may comprise a fluorinated organic solvent.

In a still further aspect, the present invention also provides a method for treating a substrate, comprising the step of applying the composition of the invention as defined above to the substrate. The obtained coating on the substrate may be cured, generally at an elevated temperature of 40 to 300° C., although elevated temperatures may not be required. The heat for curing can be supplied either through an initial preheat of substrates having sufficient heat capacity to provide the heat for curing, or through heating of coated substrates by an external heat source subsequent to coating.

The present invention further provides a composition for and a method of applying an antisoiling coating to a substrate having an antireflective surface; the method involves treating the antireflective surface with the instant coating composition. A preferred substrate is an antireflective substrate. The protective coating on an antireflective surface is relatively durable, and more resistant to contamination and easier to clean than the antireflective surface itself. The antisoiling coating is at least partially cured, i.e., solidified as by polymerizing and/or crosslinking.

The antireflective surface preferably includes a metal oxide film having one or more metal oxides, which have been preferably vacuum deposited (e.g., sputter coated). The antisoiling coating is preferably at least about 15 Angstroms thick, and preferably no greater than about 150 Angstroms thick, for a desirable balance in performance with respect to antisoiling, durability, and antireflectance. Preferably, the antireflective article has a first surface antireflectivity that is different by less than about 0.5 percentage units from that of the same article without the antisoiling coating.

BRIEF DESCRIPTION OF THE FIGURES

FIG. 1a is a digital image of an atomic force micrograph of the coated antireflective surface of Example 16a.

FIG. 1b is the associated legend showing the height of the surface features of FIG. 1a.

FIG. 2b is the associated legend showing the height of the surface features of FIG. 2a.

FIG. 3b is the associated legend showing the height of the surface features of FIG. 3a.

DETAILED DESCRIPTION OF THE INVENTION

The monovalent or divalent fluorinated group $R_f^1$ in the above Formula I, representing the fluorinated silane, can include linear, branched, and/or cyclic structures, that may be saturated or unsaturated. It is preferably a perfluorinated group (i.e., all C—H bonds are replaced by C—F bonds).

In one embodiment the $R_f^1$ includes mono- and divalent perfluoropolyethers comprising perfluorinated repeating units selected from the group of —$(C_nF_{2n})$—, —$(C_nF_{2n}O)$—, —(CF(Z))-, —(CF(Z)O)—, —(CF(Z)$C_nF_{2n}O)$—, —$(C_nF_{2n}CF(Z)O)$—, —$(CF_2CF(Z)O)$—, and combinations thereof. In these repeating units Z is a fluorine atom, a perfluoroalkyl group, an oxygen-substituted perfluoroalkyl group, a perfluoroalkoxy group, or an oxygen-substituted perfluoroalkoxy group, all of which can be linear, branched, or cyclic, and preferably have about 1 to about 9 carbon atoms and 0 to about 4 oxygen atoms. Examples of perfluoropolyethers containing polymeric moieties made of these repeating units are disclosed in U.S. Pat. No. 5,306,758 (Pellerite). For the monovalent perfluoropolyether group (wherein y is 1 in Formula I above), the terminal groups can be $(C_nF_{2n+1})$—, $(C_nF_{2n+1}O)$—or $(X'C_nF_{2n}O)$—, wherein X' is H, Cl, or Br, for example. Preferably, these terminal groups are perfluorinated. In these repeating units or terminal groups, n is 1 or more, and preferably 1 to 4.

Preferred approximate average structures for a divalent perfluoropolyether group include —$CF_2O(CF_2O)_m(C_2F_4O)_pCF_2$—; —$CF(CF_3)$ $(OCF_2CF(CF_3))_mO(C_nF_{2n})O(CF(CF_3)CF_2O)_pCF(CF_3)$—, wherein the value for n ranges from 2 to 4; —$CF_2O(C_2F_4O)_pCF_2$—; and —$(CF_2)_3O(C_4F_8O)_p(CF_2)_3$—; wherein an average value for m and p is 0 to 50, with the proviso that m and p are not simultaneously zero. Of these, particularly preferred approximate average structures are —$CF_2O(CF_2O)_m(C_2F_4O)_pCF_2$—, —$CF_2O(C_2F_4O)_pCF_2$—, and —$CF(CF_3)$ $(OCF_2CF(CF_3))_mO(C_nF_{2n})O(CF(CF_3)CF_2O)_pCF(CF_3)$—, wherein the value for n ranges from 2 to 4. Particularly preferred approximate average structures for a monovalent perfluoropolyether group include $C_3F_7O(CF(CF_3)CF_2O)_pCF(CF_3)$—and $CF_3O(C_2F_4O)_pCF_2$—wherein an average value for p is 1 to 50. As synthesized, these compounds typically include a mixture of oligomers and/or polymers, so p may be a non-integral value. The approximate average structure is the approximate average of the mixture.

In another embodiment the $R_f^1$ includes mono- and divalent perfluoroalkyl and perfluoroalkylene groups of the respective formulas $C_nF_{2n+1}$—and —$C_nF_{2n}$—, where n is 3 to 20, preferably 4 to 10. Such groups may be linear or branched, or a mixture thereof.

Suitable linking groups Q include the following structures. For the purposes of this list, each k is independently an integer from 0 to about 20, $R_1'$ is hydrogen, phenyl, or alkyl of 1 to about 4 carbon atoms, and $R_2'$ is alkyl of 1 to about 20 carbon atoms. Each structure is non-directional, i.e. —$C_kH_{2k}C(O)O$— is equivalent to —$O(O)CC_kH_{2k}$— and with the proviso that Si cannot be directly bonded to an —O—atom in Q and there must be at least 2 carbons between Si and any heteroatom in the following structures. Furthermore, in Q, the sum of the number of carbon atoms and the number of heteroatoms is at least 3.

-continued

—(CH$_2$)$_k$OC$_k$H$_{2k}$C(O)O—
—(CH$_2$)$_k$SO$_2$C$_k$H$_{2k}$C(O)O—
—(CH$_2$)$_k$SC$_k$H$_{2k}$C(O)O—
—OC(O)NR' C$_k$H$_{2k}$—
—C$_k$H$_{2k}$—OC(O)NH—
—C$_k$H$_{2k}$NR$_1$'C(O)O—
—(CH$_2$)$_k$SO$_2$NR$_1$'C$_k$H$_{2k}$C(O)O—
—C$_k$H$_{2k}$O—
—CH$_2$CH(OR$_2$')CH$_2$C(O)O—
—C$_k$H$_{2k}$NR$_1$'C$_k$H$_{2k}$—
—C$_k$H$_{2k}$—NR$_1$'C(O)NH—, and Examples of Q groups include —C(O)NH(CH$_2$)$_3$—, —SO$_2$NR$_1$'(C$_k$H$_{2k}$k)—, —CH$_2$O(CH$_2$)$_3$—, —C(O)S (CH$_2$)$_3$—,—CH$_2$OC(O)N(R)(CH$_2$)$_3$—, wherein R is H or lower alkyl group, and —(C$_n$H$_{2n}$)—, wherein n is about 3 to about 25. Preferred linking groups Q are —C(O)NH (CH$_2$)$_3$—, —CH$_2$O(CH$_2$)$_3$—, and —CH$_2$OC(O(N(R) (CH$_2$)$_3$—, when R$_f^1$ is a perfluoropolyether. Preferred linking groups Q are —SO$_2$NR$_1$'(C$_k$H$_{2k}$)—, —C$_k$H2k—where k is greater than or equal to 3, and —CH$_2$O(CH$_2$)$_3$—, when R$_f^1$ is a perfluoroalkyl or perfluoroalkylene.

Y represents a hydrolyzable group in formula (I) such as for example a halide, a C$_1$–C$_4$ alkoxy group, an acyloxy group or a polyoxyalkylene group, such as polyoxyethylene groups as disclosed in U.S. Pat. No. 5,274,159. Specific examples of hydrolysable groups include methoxy, ethoxy, propoxy, chloro, and acetoxy groups.

Compounds of Formula I generally have a molecular weight (number average) of at least about 300, and preferably, at least about 500. Perfluoropolyethers may have higher molecular weights, but the molecular weights are generally no greater than about 20,000.

Examples of preferred fluorinated silanes include, but are not limited to, the following approximate average structures: XCF$_2$O(CF$_2$O)$_m$(C$_2$F$_4$O)$_p$CF$_2$X, C$_3$F$_7$O(CF(CF$_3$)CF$_2$O)$_p$ CF(CF$_3$)X, XCF(CF$_3$) (OCF$_2$CF(CF$_3$))$_m$O(C$_n$F$_{2n}$)O(CF (CF$_3$)CF$_2$O)$_p$CF(CF$_3$)X, wherein the value for n ranges from 2 to 4, XCF$_2$O(C$_2$F$_4$O)$_p$CF$_2$X, CF$_3$O(C$_2$F$_4$O)$_p$CF$_2$X, and X(CF$_2$)$_3$O(C$_4$F$_8$O)$_p$(CF$_2$)$_3$X, wherein -X is -Q-SiY$_{3-x}$ R$_x^1$ as defined above in Formula I or a nonsilane-containing terminal group as defined above ((C$_n$F$_{2n+1}$)—, (C$_n$F$_{2n+1}$ O)—or (X'C$_n$F$_{2n}$O)—wherein X' is H, Cl, or Br), with the proviso that at least one X group per molecule is a silane. The values of m and p in these approximate average structures can vary, and may be non-integral. Preferably, average values of m and p are within a range of about 1 to about 50. As these are oligomeric or polymeric materials, such compounds exist as mixtures upon synthesis, which are suitable for use. These mixtures may also contain perfluoro chains bearing no functional groups (inert fluids) or more than two terminal groups (branched structures) as a consequence of the methods used in their synthesis. Typically, mixtures containing less than about 10% by weight of nonfunctionalized compounds (e.g., those without silane groups) can be used. Furthermore, mixtures of any of the individually listed compounds of Formula I can be used.

With respect to formula I, a preferred group of fluorinated silanes includes those where R$_f^1$ represents
—CF(CF$_3$)(OCF$_2$CF(CF$_3$))$_m$(C$_n$F$_{2n}$)O(CF(CF$_3$)CCF$_2$O)$_p$ CF(CF$_3$)—;
wherein m and p are numbers from 1 to 20;
m+p≦20; n=2 to 4,
Q represents an organic divalent linking group, wherein the sum of the number of carbon atoms and the number of heteroatoms in Q is at least 3;
R$^1$ represents a C$_1$–C$_4$ alkyl group;
Y represents a hydrolysable group; and
x is 0 or 1 and y is 1 or 2.

Again with respect to formula I, another preferred group of fluorinated silanes includes those where R$_f^1$=—CF$_2$O (CF$_2$O)$_m$(CF$_2$CF$_2$O)$_p$CF$_2$—; m+p=16 to 24; and where R$_f^1$ =CF(CF$_3$)(OCF$_2$CF(CF$_3$))$_m$O(C$_n$F$_{2n}$)O(CF(CF3)CF$_2$O)$_p$CF (CF$_3$)—; m+p=4 to 12; n=4.

Where R$_f$ is a perfluoroalkyl or perfluoroalkylene group, R$_f$ can include linear, branched, or cyclic structures, that may be saturated or unsaturated. R$_f$ may be represented by the formulae —C$_n$F$_{2n+1}$ for a perfluoroalkyl group, or by —C$_n$F$_{2n}$—for a perfluoroalkylene group, wherein n is about 4 to about 20, more preferably, about 6 to about 12, and most preferably, about 7 to about 10. With reference to Formula I (supra) the divalent Q group can include linear, branched, or cyclic structures, that may be saturated or unsaturated. Typically, suitable fluorinated silanes include a mixture of isomers (e.g., a mixture of compounds containing linear and branched perfluoroalkyl groups). Mixtures of fluorinated silanes exhibiting different values of n can also be used.

Examples of preferred fluorinated perfluoroalkylsilanes include, but are not limited to, the following: C$_7$ F$_{15}$CH$_2$OCH$_2$CH$_2$CH$_2$SiCl$_3$; C$_7$F$_{15}$CH$_2$OCH$_2$CH$_2$CH$_2$Si (CH$_3$)Cl$_2$; C$_7$F$_{15}$CH$_2$OCH$_2$CH$_2$CH$_2$SiCl(OCH$_3$)$_2$; C$_7$F$_{15}$CH$_2$OCH$_2$CH$_2$CH$_2$SiCl$_2$(OC$_2$H$_5$); C$_8$F$_{17}$SO$_2$N(Et) CH$_2$CH$_2$CH$_2$SiCl$_3$; C$_8$F$_{17}$SO$_2$N(Me)CH$_2$CH$_2$CH$_2$Si(CH$_3$) Cl$_2$; C$_4$F$_9$SO$_2$N(Me)CH$_2$CH$_2$CH$_2$SiCl$_3$; C$_4$F$_9$SO$_2$N(Me) CH$_2$CH$_2$CH$_2$Si(OCH$_3$)$_3$; C$_3$F$_7$CH$_2$OCH$_2$CH$_2$CH$_2$SiCl (OCH$_3$)$_2$; and C$_7$F$_{15}$CH$_2$OCH$_2$CH$_2$CH$_2$Si(OAc)$_3$. Mixtures of such compounds can be used if desired.

The compounds of Formula I can be synthesized using standard techniques. For example, commercially available or readily synthesized perfluoropolyether esters can be combined with a functionalized alkoxysilane, such as a 3-aminopropyltrialkoxysilane, according to U.S. Pat. No. 3,810,874 (Mitsch et al.), incorporated herein by reference. Fluorinated alkyl silanes can be prepared, for example, by the procedures taught in U.S. Pat. No. 5,274,159 (Pellerite et al.), incorporated herein by reference. Modifications of these methods are described in the Examples. Such materials may or may not need to be purified before use in a treatment composition.

The composition comprising the fluorinated silane of formula (I) is generally applied to the substrate in amounts sufficient to produce a coating that is water and oil repellent. This coating can be extremely thin, e.g. 1 to 2 molecular layers, though in practice a useful coating may be thicker, e.g. 50 or more molecular layers. Reference may be made to the Figures.

Although the inventors do not wish to be bound by theory, compounds of the above Formula I are believed to undergo hydrolysis to silanols, condensation reactions with silanols or other hydroxyl groups on the substrate surface, and crosslinking to form a siloxane layer. In this way, the silanes are covalently attached to the substrate and to adjacent silane groups to form a 3-dimensional network of siloxane bonds, with attached fluorinated groups.

In this context, "siloxane" refers to —Si—O—Si—bonds to which are attached perfluoro segments (such as the R$_f^1$ groups in Formula I herein), preferably, perfluoropolyether or perfluoroalkyl segments, bonded to the silicon atoms through organic linking groups (such as the Q groups in Formula I herein). A coating prepared from a coating composition that includes compounds of Formula I can also include unreacted or uncondensed silanol groups.

For the preparation of a durable coating, sufficient water should be present in order to cause hydrolysis of the silane end groups, and condensation of the resulting silanol groups on and to the substrate. This water may be added to the composition, or to one of the constituents of the composition if stored separately and combined prior to application. If the constituents are stored separately and combined just prior to application, it is preferred that the water be combined with a constituent other than the compressed fluid carbon dioxide, due to the limited solubility of water therein. Alternatively, the water may be present on the surface of the substrate prior to application, or one may rely on ambient moisture to effect the curing. Generally, no more that two molar equivalents of water are necessary, relative to the molar amount of silane groups present.

The compositions of the invention preferably include an organic or inorganic acid. Such acids promote curing of the silane and promote adhesion of the silane to substrate surfaces, such as siliceous surfaces. Organic acids include acetic acid, formic acid, and the like; fluorinated organic acids, such as $CF_3SO_3H$, $C_3F_7COOH$, $C_7F_{15}COOH$, $C_6F_{13}P(O)(OH)_2$, or those which can be represented by the Formula II (II)

wherein $R_f^2$ represents a mono or divalent polyfluoropolyether group, L represents a covalent bond or an organic divalent linking group, Z represents an acid group, such as a carboxylic, phosphonic or phosphoric acid group; m is 0 or 1, and n is 1 or 2.

Examples of suitable $R_f^2$ groups include those given above for $R^1_f$. Examples of organic acids of Formula II include $C_3F_7O(CF(CF_3)CF_2O)_{10-30}CF(CF_3)COOH$, commercially available from DuPont as KRYTOX™ 157 FSH™, 157 FSL™, and 157 FSM™, $CF_3(CF_2)_2OCF(CF_3)COOH$, and FOMBLIN™ Z-DIAC™, a perfluoropolyether diacid available from Ausimont. Examples of inorganic acids include sulfuric acid, hydrochloric acid, phosphonic, phosphoric acid, and the like. Alternatively, the catalyst may take the form of an acid precursor which releases an acid upon exposure to heat, ultraviolet light, visible light, electron beam irradiation, or microwave irradiation. Such acid precursors include, for instance, sulfonium and iodonium salts as well as alkyl esters of alkane- or fluoroalkane-sulfonic acids, and are described in WO 98/40439.

The acid or acid precursor will generally be included in the composition in an amount between about 0.0005 and 10%, more preferably between 0.001 and 5% by weight. Alternatively, the substrate may be first treated with the fluorochemical silane, and then treated with acid to promote curing of the silane. The acid may be applied neat, but is preferably applied as a solution in water or in an organic solvent.

A composition of the present invention may comprise one or more organic solvents. The organic solvent or blend of organic solvents used must be capable of dissolving at least 0.01% by weight of the fluorinated silane of Formula I. Furthermore, the solvent or mixture of solvents should have a solubility in compressed fluid carbon dioxide of at least 0.01%, preferably at least 1% by weight and a solubility for acid (if present) of at least 0.01% by weight. If the organic solvent or mixture of organic solvents do not meet these criteria, it may not be possible to obtain a homogeneous mixture of the fluorinated silane, carbon dioxide, and (optional) acid. Although such non-homogeneous compositions could be used to treat a substrate, the coating obtained therefrom may not have the desired oil/water repellency and may not have sufficient durability properties.

Suitable organic solvents, or mixtures of solvents can be selected from aliphatic alcohols, such as methanol, ethanol, and isopropyl alcohol; ketones such as acetone or methyl ethyl ketone; esters, such as ethyl acetate or methyl formate; and ethers, such as diisopropyl ether. Fluorinated solvents may be used alone or in combination with the organic solvents in order to improve solubility and/or viscosity properties of the fluorinated silane, or as a levelling agent.

Examples of fluorinated solvents include fluorinated hydrocarbons, such as perfluorohexane or perfluorooctane, available from 3M; partially fluorinated hydrocarbons, such as pentafluorobutane, available from Solvay, or $CF_3CFHCFHCF_2CF_3$, available from DuPont; and hydrofluoroethers, such as methyl perfluorobutyl ether or ethyl perfluorobutyl ether, or $C_3F_7CF(OC_2H_5)CF(CF_3)_2$, available from 3M. Various blends of these materials with organic solvents can be used.

The compositions may contain further components such as, for example, one or more hydrocarbon silanes, i.e. silanes that are substantially non-fluorinated. However, the addition of hydrocarbon silanes is preferably kept below about 50% by weight, in order not to adversely affect the oil repellency properties of the composition.

Suitable substrates that can be treated in a particularly effective way with the fluorinated silane mixture of this invention include substrates having a hard surface preferably with functional groups, such as —OH groups that occur on siliceous substrates, capable of reacting with the fluorinated silane according to formula (I). Preferably, such reactivity of the surface of the substrate is provided by functional groups having active hydrogen atoms, such as —OH. When such active hydrogen atoms are not present, the substrate may first be treated in a plasma containing oxygen or in a corona atmosphere to make it reactive to the fluorinated silane.

Treatment of the substrates results in rendering the treated surfaces less retentive of soil and more readily cleanable due to the oil and water repellent nature of the treated surfaces. These desirable properties are maintained despite extended exposure or use and repeated cleanings because of the high degree of durability of the treated surface as can be obtained through the compositions of this invention.

Preferably, the substrate should be clean prior to applying the compositions of the invention so as to obtain optimum characteristics, particularly durability. That is, the surface of the substrate to be coated should be substantially free of organic contamination prior to coating. Cleaning techniques depend on the type of substrate and include, for example, a solvent washing step with an organic solvent, such as acetone or ethanol, or a reactive gas-phase treatment such as air plasma or UV/ozone.

Useful substrates include ceramics, glazed ceramics, glass, metal metals (such as aluminum, iron, stainless steel, copper and the like), natural and man-made stone, thermoplastic materials (such as poly(meth)acrylate, polycarbonate, polystyrene, styrene copolymers such as styrene/acrylonitrile copolymers, and polyesters such as polyethylene terephthalate), paints (such as those based on acrylic resins), powder coatings (such as polyurethane, epoxy or hybrid powder coatings), and wood.

Particularly preferred substrates include those siliceous substrates including ceramics, glazed ceramics, glass, concrete, mortar, grout and natural and man-made stone. Various articles can be effectively treated with the fluorochemical solution of the present invention to provide a water and oil repellent coating thereon. Examples include ceramic tiles, bathtubs or toilets, glass shower panels, construction glass, various parts of a vehicle (such as the mirror or windscreen), glass, and ceramic or enamel pottery materials.

A preferred substrate is an antireflective substrate. Antireflective (AR) surfaces or substrates prepared by vacuum sputtering of metal oxide thin films on substrates made of glass or plastic are particularly useful in display devices of electronic equipment. Such metal oxide films are relatively porous and consist of clusters of particles forming a relatively rough profile. Such coatings help reduce glare and reflection. When they are conductive coatings, they also help reduce static discharge and electromagnetic emissions. Thus, the primary application for these coatings is to provide contrast enhancement and antireflective properties to improve the readability of display devices, such as computer monitors. Antireflective substrates are described in U.S. Pat. No. 5,851,674 (Pellerite et al.) incorporated by reference herein in its entirety.

Sputtered metal oxide antireflective coatings are generally durable and uniform. Also, their optical properties are controllable, which makes them very desirable. They also have very high surface energies and refractive indices. However, the high surface energy of a sputtered metal oxide surface makes it prone to contamination by organic impurities (such as skin oils). The presence of surface contaminants results in a major degradation of antireflectivity properties of the metal oxide coatings. Furthermore, because of the high refractive indices, surface contamination becomes extremely noticeable to the end-user.

The present invention provides a protective coating on an antireflective surface that is relatively durable, and more resistant to contamination and easier to clean than the antireflective surface itself. The present invention provides in one embodiment a method and composition for use in preparing an antireflective article comprising a substrate having an antireflective surface and an antisoiling coating of less than about 100 Angstroms thick deposited thereon. The antisoiling coating comprises a fluorinated siloxane film of a thickness that does not substantially change the antireflective characteristics of the antireflective article. The fluorinated siloxane is prepared by applying and curing a coating composition comprising a fluorinated silane of the above formulas in compressed fluid carbon dioxide. In one embodiment, the method comprises treating the antireflective surface with a coating composition comprising a fluorinated silane in compressed fluid carbon dioxide without subsequent mechanical processing of the treated substrate to remove excess coating material. Another method of applying an antisoiling coating to a substrate having an antireflective surface consists essentially of spraying the antireflective surface with a fluorinated silane in compressed fluid carbon dioxide coating composition comprising less than about 0.5 weight percent of a fluorinated silane represented by the above formula (I).

Preferably, the overall coating thickness of the antisoiling coating is greater than a monolayer (which is typically greater than about 15 Angstroms thick). That is, preferably, an antisoiling coating of the present invention is at least about 20 Angstroms thick, and more preferably, at least about 30 Angstroms thick. Preferably, it is less than about 100 Angstroms thick, and more preferably, less than about 50 Angstroms thick. The coating material is typically present in an amount that does not substantially change the antireflective characteristics of the antireflective article.

The coating composition is typically a relatively dilute solution, containing between 0.01 and 5 percent by weight inclusive of the fluorinated silane, more preferably, between 0.03 and 3 percent by weight inclusive of the fluorinated silane, and most preferably, between 0.05 and 0.2 percent by weight inclusive of the fluorinated silane. The ratio of the co-solvents (if any), $CO_2$ and acid should be chosen so as to obtain a homogeneous mixture.

For ease of manufacturing and for reasons of cost, the compositions of the present invention will generally be prepared shortly before use by diluting a concentrate of the fluorinated silane of formula (I) in compressed fluid carbon dioxide. The concentrate will generally comprise a solution of the fluorinated silane of formula (I) in an organic solvent with or without acid being present in such concentrate. The concentrate should be stable for several weeks, preferably at least 1 month, more preferably at least 3 months.

Thus, in accordance with a preferred embodiment, compositions for application to a substrate are prepared by diluting a fluorinated silane according to Formula I in $CO_2$, optionally adding to the mixture an organic solvent or mixture of solvents, and optionally an acid catalyst. A freshly prepared diluted solution in $CO_2$ will generally be stable for 1 or more days. In another embodiment, the $CO_2$ and fluorochemical silane may be separately stored, and combined immediately prior to application, by means of a mixing chamber in which measured amounts of the two streams are combined. The acid, if present, may be combined with either the $CO_2$ or the fluorochemical silane prior to mixing of the two streams.

A preferred coating method for application of a composition of the present invention includes spray application. Spraying may be effected by passing the pressurized mixture through a suitable jet, nozzle or orifice onto the substrate surface in the form of a stream or atomized mist. Generally, the pressure drop between the pressurized mixture and the application environment causes rapid evaporation of the $CO_2$ prior to contact with the substrate surface, resulting in deposition of an extremely thin, uniform coating of the fluorochemical silane. Where solvents are used in the composition, they may promote uniform spreading of the fluorinated silane over the substrate surface, and evaporate readily.

Equipment useful in spraying the fluorochemical silane is described in U.S. Pat. No. 5,027,742 and U.S. Pat. No. 4,923,720 (Lee et al.), U.S. Pat. No. 5,066,522 (Cole et al.), U.S. Pat. No. 5,108,799 and U.S. Pat. No. 5,211,342 (Hoy et al.), incorporated herein by reference. Reference may also be made to Lewis, Argyropoulos and Nielson, "Supercritical Carbon Dioxide Spray Systems", *Metal Finishing*, Apr., 1997. In one useful spray system, the fluorochemical silane is fed from a first reservoir to the suction side of a metering gear pump. Supercritical carbon dioxide is fed from a second reservoir that may be provided with a pressure controller and heating coil to adjust the pressure to the desired level. The carbon dioxide is fed through the pressure controller to the input side of the metering pump in amounts sufficient to bring the composition into the desired composition range. The mixture of the fluorinated silane and carbon dioxide may then be fed through a mixing device until homogeneous. Thereafter, the mixture may then be heated through a heat exchanger to avoid condensation of carbon dioxide and ambient water vapor. The mixture is then forced out a nozzle where atomization takes place.

A substrate to be coated can typically be contacted with the treating composition at room temperature (typically, about 20° C. to about 25° C.). Alternatively, the mixture can be applied to substrates that are preheated at a temperature of for example between 60° C. and 150° C. This is of particular interest for industrial production, where e.g. ceramic tiles can be treated immediately after the firing oven at the end of the production line. Following application, the treated substrate can be dried and cured at ambient or elevated temperature, e.g. at 40° to 300° C. and for a time sufficient to dry or cure.

Significantly, for preferred embodiments of the present invention, substantially no post-treatment of the coating, such as polishing or solvent washing, is necessary to achieve the desired antisoiling characteristics or to restore optical properties or gloss. Certain conventional spray methods may require a polishing or solvent washing step after coating to remove excess material that can detrimentally affect the optical properties of the finished article.

Materials:

FC-4:
N-methylperfluorobutanesulfonamidopropyltrimethoxysilane: $C_4F_9SO_2N(CH_3)C_3H_6Si(OCH_3)_3$; (prepared essentially as in U.S. Pat. No. 5,274,159; Ex 6)

FC-8:
N-ethylperfluorooctanesulfonamidopropyltrimethoxysilane; $C_8F_{17}SO_2N(C_2H_5)C_3H_6Si(OCH_3)_3$; (prepared essentially as in U.S. Pat. No. 5,274,159; Ex 6)

FC-2202™:
$HOCH_2CF_2(CF_2O)_n(CF_2CF_2O)_mCF_2CH_2OH$; where n, m=~10; (available from 3M Company, St. Paul, Minn.).

Fomblin Z-DEAL™:
$CH_3OC(O)CF_2(CF_2O)_n(CF_2CF_2O)_mCF_2C(O)OCH_3$; where n, m=~10 (available from Ausimont, Thorofare, N.J.)

Fomblin Z-DIAC™:
$HOC(O)CF_2(CF_2O)™(CF_2CF_2O)_mCF_2C(O)OH$; where n, m=~10 (available from Ausimont, Thorofare, N.J.)

KRYTOX 157 FSL:
$C_3F_7O(CF(CF_3)CF_2O)_nCF(CF_3)COOH$, $n_{avg}$ ~13 (available from DuPont Co., Wilmington, Del.).

HFE-7100™:
$C_4F_9OCH_3$ perfluorobutyl methyl ether; (3M™ NOVEC™ HFE-7100; available from 3M Company, St. Paul, Minn.).

HFE-7500:
$C_3F_7CF(OC_2H_5)CF(CF_3)_2$; (3M™ NOVEC™ HFE-7500; available from 3M Company, St. Paul, Minn.).

PFPE Disilane:
$(CH_3O)_3SiCH_2CH_2CH_2NHC(O)CF_2(CF_2O)_n$ $(CF_2CF_2O)_m\ CF_2C(O)NH\ —CH_2CH_2CH_2Si(OCH_3)_3$; where n, m=~10, prepared as described in U.S. Pat. No. 3,810,874

PFPE-EA:
$HO(C_2H_4)NHC(O)CF_2(CF_2O)_n(CF_2\ CF_2O)_mCF_2C(O)$ $NH(C_2H_4)OH$; where n, m=~10 (as prepared in Example 15)

PFPE Monosilane:
$CF_3O(CF_2CF_2O)_{12}CF_2CONHC_3H_6Si(OEt)_3$ prepared as described in WO 99/37720.

HFPO Disilane:
$(CH_3O)_3Si(CH_2)_3NHC(O)OCH_2—CF(CF_3)\ (OCF_2CF(CF_3))_mO(C_nF_{2n})O(CF(CF_3)CF_2O)\ _pCF(CF_3)CH_2OC(O)$ $NH(CH_2)_3Si(OCH_3)_3$, where m, p=~1–3, n=4. The precursor diol was prepared as described as in U.S. Pat. No. 3,574,770, and subsequently reacted with two equivalents of isocyanatopropyltrimethoxysilane.

Application and Test Methods

Carbon Dioxide Spray Process

Fluorochemical compositions were applied onto substrates via a carbon dioxide spray process. The spraying apparatus was a locally constructed 10 mL volume stainless steel view cell equipped with sapphire windows, temperature controlling unit, a pressure handling system, a cylinder of liquid carbon dioxide, pressure transducer, and, optionally, a pressure generator for adjustment of cell pressure. The view cell was connected to high pressure capillary stainless steel tubing (1/16" OD, 0.030" ID) with an in-line needle valve. The contents of the cell were sprayed onto the substrates by manually controlling the opening of the needle valve and manually moving the substrates in front of the spray stream at the needle valve. In some cases the contents of the cell were heated slightly prior to spraying, while other experiments were conducted at ambient temperature. The cell pressure was maintained during spray by providing back pressure from the carbon dioxide cylinder.

Dip-Coating Process

As a comparison to the inventive carbon dioxide spray-coating process described above, comparative samples were dip-coated with diluted aliquots from the same formulations previously sprayed from carbon dioxide. Dip-coated films were obtained by dipping samples in a coating solution and subsequently lowering the solution at a constant rate (100 mm min$^{-1}$) using a locally constructed dip-coating machine. Some of the samples were treated with a coating solution which contained an acid catalyst, i.e., acetic acid or FOMBLIN™ Z_DIAC. Upon drying, these samples were immediately cured in a 115° C. oven for 20 minutes. For solutions which did not contain an acid catalyst, the samples were submerged in a 3% aqueous acetic acid solution for three minutes. These samples were then rinsed with water and subsequently cured in a 115° C. oven for 20 minutes. Upon cooling to room temperature, all of the samples were lightly buffed using a paper towel wetted with HFE 7100 to remove any excess coating material.

Post Application Treatment

Samples prepared with acid catalyst in-situ with the fluorochemical were cured by heating the treated substrate in a 115° C. oven for 20 minutes. Upon cooling to room temperature, the substrates were lightly buffed with HFE 7100 using a paper towel, a Kimwipe™ or a 3M High Performance Wipe™ to remove excess coating material. Samples which did not contain the acid catalyst within the solution were post-treated by submerging the treated substrates in a 3% aqueous acetic acid solution for 3 minutes. The samples were then rinsed with water and subsequently cured at 115° C. for 20 minutes, cooled to ambient temperature, followed by a light buffing with HFE 7100.

Abrasion/Scrub Test

Using a nylon bristle brush (ASTM# D2486; 5/4×13 row pattern) loaded @ 435 gram, samples were subjected to varied numbers of scrub cycles performed on a reciprocating motion machine.

Contact Angle Measurement

In order to evaluate the repellency of the treated samples, static water and hexadecane contact angle measurements were made using a Kruss G10 goniometer. Deionized water or hexadecane was allowed to equilibrate for one minute prior to measurement. For each sample, five individual water or hexadecane drops were analyzed; average contact angles and standard deviations were calculated. Larger values of contact angles indicate better repellency.

EXAMPLES

Example 1

Spray coating of FC-8. FC-8 (0.58 grams; 0.842 mmole) was placed in the 10 mL view cell and pressurized to 2030 psi (140 bar) at 21° C. with carbon dioxide. FC-8 and carbon dioxide became immediately and completely miscible, forming one clear liquid phase. The mixture was sprayed onto a ceramic tile according to the procedure described in the Carbon Dioxide Spray Process section above. Since freezing of the exit line occurred during the spray process the needle valve was closed and the cell was heated to 50° C. After several minutes, the needle valve was opened and the mixture was then sprayed onto several glass microscope slides. The samples were then treated according to the general procedure described in the Post Application Treatment section above.

Example 2

Spray coating of acid-catalyzed FC-8 in HFE-7100. Example 2 is essentially Example 1, with the exception that an acid catalyzed solution containing FC-8 (20%), acetic acid (1%) and HFE-7100 (79%) was prepared, and 0.88 grams of this acid catalyzed solution was placed in the 10 mL view cell. Results of water contact angle measurements are listed in Table 1.

Example 2A

Dip coating of acid-catalyzed FC-8 in HFE-7100. An aliquot of the acid catalyzed solution (10.0 g) prepared in Example 2 was further diluted with HFE-7100 (90.0 g) to yield a solution containing FC-8 (2.0%), acetic acid (0.1%) and HFE-7100 (97.9%). This diluted solution was used to coat glass microscope slides according to the methods outlined in the Dip-Coat Method section above. Results of water contact angle measurements are listed in Table 1.

Example 3

Spray coating of FC-8 in HFE-7100. Example 3 is essentially Example 1, with the exception that a solution containing FC-8 (2%), and HFE-7100 (98%) was prepared, and 0.61 grams of this solution was placed in the 10 mL view cell. Results of water contact angle measurements are listed in Table 1.

Example 3A

Dip coating of FC-8 in HFE-7100. An aliquot of the solution prepared in Example 3 (10.0 g) was further diluted with HFE-7100 (90.0 g) to yield a solution containing FC-8 (0.15%), and HFE-7100 (99.85%). This diluted solution was used to coat glass microscope slides according to the methods outlined in the Dip-Coat Method section above. Results of water contact angle measurements are listed in Table 1.

TABLE 1

| | Water Contact Angle, deg (std. dev) |
|---|---|
| Example 2 | 102 (1) |
| Example 3 | 106 (4) |
| Example 2A | 95 (4) |
| Example 3A | 99 (3) |

Example 4

Spray coating of acid-catalyzed PFPE disilane in HFE-7100. Example 4 is essentially Example 1, with the exception that the FC-8 solution is replaced with an acid catalyzed solution containing PFPE disilane (1.0%), FOMBLIN Z-DIAC acid catalyst (0.1%) and HFE-7100 (98.9%) and 1.0 mL of this acid catalyzed solution was placed in the 10 mL view cell. The cell was pressurized to 1880 psig (130 bar) at 25° C. with carbon dioxide. The resulting mixture appeared slightly hazy throughout, but evenly dispersed in the cell. Water contact angle measurements are listed in Table 2.

Example 4A

Dip coating of acid-catalyzed PFPE disilane in HFE-7100. An aliquot of the solution prepared in Example 4 (10.0 g) was further diluted with HFE-7100 (90.0 g) to yield a solution containing PFPE disilane (0.1%), FOMBLIN Z-DIAC acid catalyst (0.01%) and HFE-7100 (98.9%). This diluted solution was used to coat glass microscope slides according to the methods outlined in the Dip-Coat Method section above. Water contact angle measurements are listed in Table 2.

Example 5

Spray coating of PFPE disilane in HFE-7100. Example 5 is essentially Example 1, with the exception that the FC-8 solution is replaced with a solution containing PFPE disilane (1.0%), and HFE-7100 (99.0%) and 1.0 mL of this solution was placed in the 10 mL view cell. The cell was pressurized to 1960 psig (135 bar) at 38° C. with carbon dioxide. The resulting mixture appeared clear. Water contact angle measurements are listed in Table 2.

Example 5A

Dip coating of PFPE disilane in HFE-7100. An aliquot of the solution (10.0 g) prepared in Example 5 was further diluted with HFE-7100 (90.0 g) to yield a solution containing PFPE disilane (0.1%), and HFE-7100 (99.9%). This diluted solution was used to coat glass microscope slides according to the methods outlined in the Dip-Coat Method section above. Water contact angle measurements are listed in Table 2.

Example 6

Spray coating of acid-catalyzed FC-8 in HFE-7100. Example 6 is essentially Example 1, with the exception that an acid catalyzed solution containing FC-8 (10%), FOMBLIN Z-DIAC (1%), and HFE-7100 (89%) was prepared, and 1.0 mL of this acid catalyzed solution was placed in the 10 mL view cell. Results of water contact angle measurements are listed in Table 2.

Example 6A

Dip coating of Acid-catalyzed FC-8 in HFE-7100. An aliquot of the acid catalyzed solution prepared in Example 6 (1.0 g) was further diluted with HFE-7100 (99.0 g) to yield a solution containing FC-8 (0.10%), FOMBLIN Z-DIAC (0.01%) and HFE-7100 (99.89%). This diluted solution was used to coat glass microscope slides according to the methods outlined in the Dip-Coat Method section above. Results of water contact angle measurements are listed in Table 2.

Example 7

Spray coating of FC-8 in HFE-7100. Example 7 is essentially Example 1, with the exception that a solution of FC-8 (10%) and HFE-7 100 (90%) was prepared, and 1.0 mL of this solution was placed in the 10 mL view cell. Results of water contact angle measurements are listed in Table 2.

Example 7A

Dip coating of FC-8 in HFE-7100. An aliquot of the solution (1.0 g) prepared in Example 7 was further diluted with HFE-7100 (99.0 g) to yield a solution containing FC-8 (0.1%), and HFE-7100 (99.9%). This diluted solution was used to coat glass microscope slides according to the methods outlined in the Dip-Coat Method section above. Results of water contact angle measurements are listed in Table 2.

TABLE 2

| Sample | Acid-treatment | Water Contact Angle (°) |
|---|---|---|
| Spray-coat | | |
| Example 4 | In situ acid | 103 |
| Example 4 | In situ acid | 100 |
| Example 5 | Post-acid treatment | 107 |
| Example 5 | Post-acid treatment | 106 |
| Example 6 | In situ acid | 106 |
| Example 6 | In situ acid | 101 |
| Example 7 | Post-acid treatment | 105 |
| Example 7 | Post-acid treatment | 105 |
| Dip-coat | | |
| Example 4A | In situ acid | 101 |
| Example 5A | Post-acid treatment | 105 |
| Example 6A | In situ acid | 89 |
| Example 7A | Post-acid treatment | 104 |

All compositions listed in Table 2. exhibited acceptable values for water contact angles. Carbon dioxide-delivered coatings were at least comparable to and in some cases superior to dip-coated samples.

Example 8

Spray coating of FC-4 in HFE-7100. 1.0 mL of a solution of FC-4 (1 wt % in HFE-7100) was placed in the 10 mL view cell and pressurized with carbon dioxide to 1725 psig (119 bar). The FC-4 and carbon dioxide became immediately and completely miscible, forming one clear liquid phase. The cell was heated to 40° C. (2340 psig or 161 bar). The sample was spray-coated onto an acetone-wiped glass slide (1), degreased galvanized steel plate (2), and aluminum plate (3). These spray-coated hard substrates (1–3) were post-treated with acid catalyst as described in the Post Application Treatment section above, and their respective contact angles were measured and are listed in Table 3.

Example 8A

Dip coating of FC-4 in HFE-7100. An aliquot of the solution (10.0 g) prepared in Example 8 was further diluted with HFE-7100 (90.0 g) to yield a solution containing FC-4 (0.1%), and HFE-7100 (99.9%). This diluted solution was used to coat a glass microscope slide, galvanized steel plate and aluminum plate according to the methods outlined in the Dip-Coat Method section above; their respective contact angles were measured and are listed in Table 3.

Example 9

Spray coating of FC-8 in HFE-7100. 1.0 mL of a solution of FC-8, (1.0 mL of a 1.0 wt % in HFE-7100) was placed in the 10 mL view cell and pressurized with $CO_2$ to 1725 psig (119 bar), giving a clear solution. The cell was heated to 40° C. (2340 psig; 161 bar). The sample was spray-coated onto an acetone-wiped glass slide (1), degreased galvanized steel plate (2) and aluminum plate (3). The spray-coated hard substrates (1–3) were post-treated as described in the Post Application Treatment section above, and their respective water contact angles were measured and are listed in Table 3.

Example 9A

Dip-Coating of FC-8 in HFE-7100. An aliquot of the solution (10.0 g) prepared in Example 9 was further diluted with HFE-7100 (90.0 g) to yield a solution containing FC-8 (0.1%), and HFE-7100 (99.9%). This diluted solution was used to coat glass microscope slides, galvanized steel plate and aluminum plate according to the methods outlined in the Dip-Coat Method section above, and their respective contact angles were measured and are listed in Table 3.

Example 10

A 1.0 mL aliquot of a solution of PFPE disilane, (1 wt % in HFE-7100) was placed in the 10 mL view cell and pressurized with carbon dioxide to 1925 psig (133 bar; 39° C.). The resulting mixture was slightly hazy throughout. The sample was spray-coated onto an acetone-wiped glass slide (1), degreased galvanized steel plate (2) and aluminum plate (3). The spray-coated hard substrates (1–3) were post-treated as described in the Post Application Treatment section above and their respective contact angles were measured and are listed in Table 3.

Example 10A

Dip-Coating of PFPE disilane in HFE-7100. An aliquot of the solution (10.0 g) prepared in Example 10 was further diluted with HFE-7100 (90.0 g) to yield a solution containing PFPE disilane (0.1%), and HFE-7100 (99.9%). This diluted solution was used to coat glass microscope slides, galvanized steel plate and aluminum plate according to the methods outlined in the Dip-Coat Method section above; their respective contact angles were measured and are listed in Table 3.

TABLE 3

| | Contact Angle Data (°) | | |
|---|---|---|---|
| Sample | Glass Slide | Galv. Steel Plate | Aluminum Plate |
| Spray-coat | | | |
| Example 8 | 100 | 93 | 92 |
| Example 9 | 101 | 109 | 98 |
| Example 10 | 101 | 117 | 75 |
| Dip-coat | | | |
| Example 8A | 91 | 87 | 85 |
| Example 9A | 103 | 100 | 85 |
| Example 10A | 108 | 103 | 95 |

Example 11

Spray coating of PFPE monosilane in HFE-7100. Example 11 was essentially as in Example 1, with the exception that a solution containing PFPE monosilane (1.0%), and HFE-7100 (99.0%) was prepared, and 1.0 mL of this solution was placed in the 10 mL view cell. The spray-coated glass was post-treated as described in the Post Application Treatment section above; respective contact angles were measured and are listed as initial values in Table 4. In addition, durability of the coatings was measured by repeating the contact angle measurements after 250 scrub cycles and after 500 scrub cycles, according to the abrasion test described above. The durability results are listed in Table 4.

Example 12

Spray coating of acid catalyzed PFPE Disilane in HFE-7100. Example 12 is essentially Example 1, with the exception that a solution containing PFPE Disilane (1.0%), FOMBLIN™ Z-DIAC acid catalyst (0.1%) and HFE-7100 (98.9%) was prepared, and 1.0 mL of this solution was placed in the 10 mL view cell. The spray-coated glass was post-treated as described in the Post Application Treatment section above; respective contact angles were measured and are listed as initial values in Table 4. In addition, durability of the coatings was measured by repeating the contact angle measurements after 250 scrub cycles and after 500 scrub cycles, according to the abrasion test described above. The durability results are listed in Table 4.

Example 13

Spray coating of HFPO disilane in HFE-7100. Example 13 is essentially Example 1, with the exception that a solution containing HFPO disilane (1.0%), and HFE-7100 (99.0%) was prepared, and 1.0 mL of this solution was placed in the 10 mL view cell. The spray-coated glass was post-treated as described in the Post Application Treatment section above; respective contact angles were measured and are listed as initial values in Table 4. In addition, durability of the coatings was measured by repeating the contact angle measurements after 250 scrub cycles and after 500 scrub cycles, according to the abrasion test described above. The durability results are listed in Table 4.

Example 14

Spray coating of FC-4 in HFE-7100. Example 14 is essentially Example 1, with the exception that a solution of FC-4 (1.0%), and HFE-7100 (99.0%) was prepared, and 1.0 mL of this solution was placed in the 10 mL view cell. The spray-coated glass was post-treated as described in the Post Application Treatment section above; respective contact angles were measured and are listed as initial values in Table 4. In addition, durability of the coatings was measured by repeating the contact angle measurements after 250 scrub cycles and after 500 scrub cycles, according to the abrasion test described above. The durability results are listed in Table 4.

Example 15

Synthesis of PFPE-EA. PFPE-EA was prepared by reacting 2 equivalents of ethanolamine with 1 eq. of Fomblin Z-DEAL. The reaction was run neat at atmospheric temperature and pressure under an inert atmosphere of nitrogen. A near quantitative yield of >99% of PFPE-EA was obtained.

TABLE 4

| Description | Initial | 250 scrubs | 500 Scrubs |
| --- | --- | --- | --- |
| Example 11 | | | |
| Water | 107.0 (2.3) | 85.8 (5.0) | 83.2 (9.3) |
| Hexadecane | 72.8 (1.1) | 43.7 (4.3) | 34.3 (4.7) |
| Example 12 | | | |
| Water | 97.9 (2.4) | 89.1 (3.2) | 83.4 (10.5) |
| Hexadecane | 65.4 (0.6) | 45.4 (2.7) | 36.6 (3.5) |
| Example 13 | | | |
| Water | 112.9 (1.1) | 109.8 (0.7) | 110.8 (0.6) |
| Hexadecane | 71.2 (0.7) | 69.0 (1.5) | 67.3 (2.8) |
| Example 14 | | | |
| Water | 100.5 (2.3) | 89.7 (4.3) | 83.4 (2.3) |
| Hexadecane | 54.7 (2.5) | 28.2 (3.5) | 27.9 (6.7) |

Example C1

1H,1H,2H,2H-perfluorodecyltriethoxysilane in HFE-7100. Example C1 is essentially Example 1, with the exception that a solution containing 1H,1H,2H,2H-perfluorodecyltriethoxysilane (1.0%; available from ABCR chemicals, Karlsruhe, Germany; Product #F059H) and HFE-7100 (99.0%) was prepared, and 1.0 mL of this solution was placed in the 10 mL view cell. Results of water and hexadecane contact angle measurements are listed in Table 5.

Example C2

FC-2202 in HFE-7100. Example C2 is essentially Example 1, with the exception that a solution containing FC-2202 (1.0%; available from 3M, St Paul, Minn.) and HFE-7100 (99.0%) was prepared, and 1.0 mL of this solution was placed in the 10 mL view cell. Results of water and hexadecane contact angle measurements are listed in Table 5.

Example C3

PFPE-EA in HFE-7100. Example C3 is essentially Example 1, with the exception that a solution containing PFPE-EA (1.0%; see Example 15) and HFE-7100 (99.0%) was prepared, and 1.0 mL of this solution was placed in the 10 mL view cell. A hazy solution was observed upon charging the cell with carbon dioxide. Results of water and hexadecane contact angle measurements are listed in Table 5.

Example C4

Fomblin Z-DEAL in HFE-7100. Example C4 is essentially Example 1, with the exception that a solution containing Fomblin Z-DEAL (1.0%; available from Ausimont, Thorofare, N.J.) and HFE-7100 (99.0%) was prepared, and 1.0 mL of this solution was placed in the 10 mL view cell. . Results of water and hexadecane contact angle measurements are listed in Table 5.

Example C5

KRYTOX 157 FSL in HFE-7100. Example C5 is essentially Example 1, with the exception that a solution containing KRYTOX 157 FSL (1.0%) and HFE-7100 (99.0%) was prepared, and 1.0 mL of this solution was placed in the 10 mL view cell. Results of water and hexadecane contact angle measurements are listed in Table 5.

Example 16

Figure 3A:
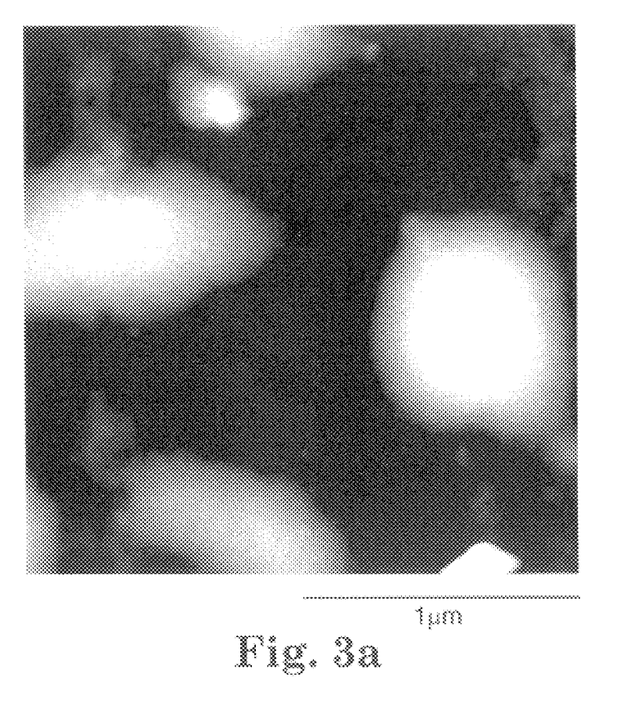
FIG. 3a is a digital image of an atomic force micrograph of the coated antireflective surface of Example 16.
Figure 3B:
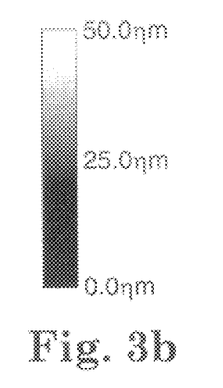

PFPE disilane/HFE-7100 solution with no acid catalyst added. 1.0 mL of a solution of PFPE disilane (1 wt %), and HFE-7100 (99.0 wt %) was placed in the 10 mL view cell and pressurized with carbon dioxide. The cell was heated to 40° C. The mixture was hazy throughout. The sample was spray-coated onto microscope glass slides and antireflective glass. Durability of the coatings on glass microscope slides was measured by repeating the contact angle measurements after buffing and after 1000 scrub cycles, according to the abrasion test described above. Results of water and hexadecane contact angle measurements are listed in Table 5. FIG. 3a is an AFM of the surface of this treated antireflective glass (product designated CDAR/CDAR, available from Viratec Thin Films, Faribault, Minn.). This image shows an example of an excessively thick coating which severely disrupts the antireflective properties of the substrate antireflective glass, although the coating still exhibits antisoiling properties.

Example 16A

Figure 1A:
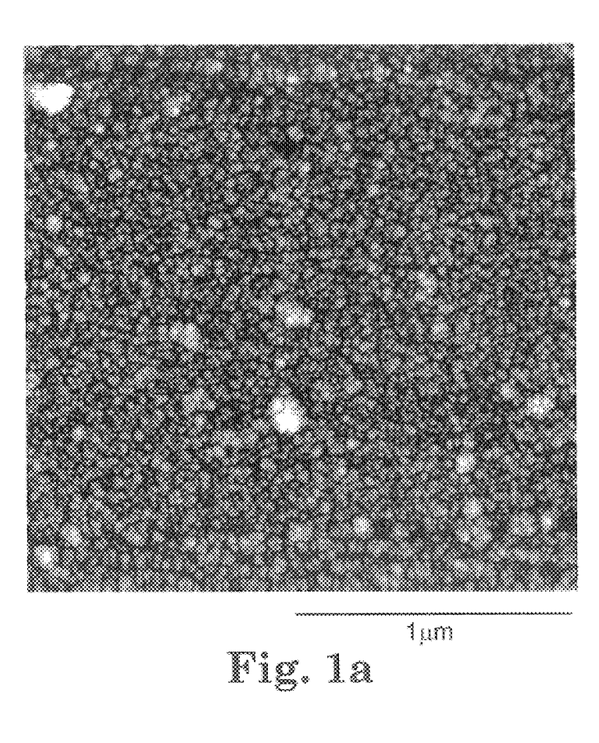
Figure 1B:
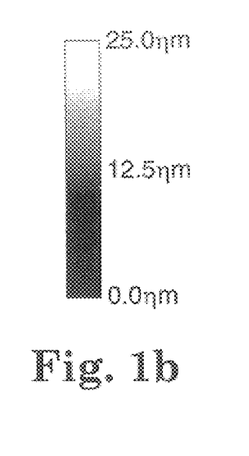
Figure 2A:
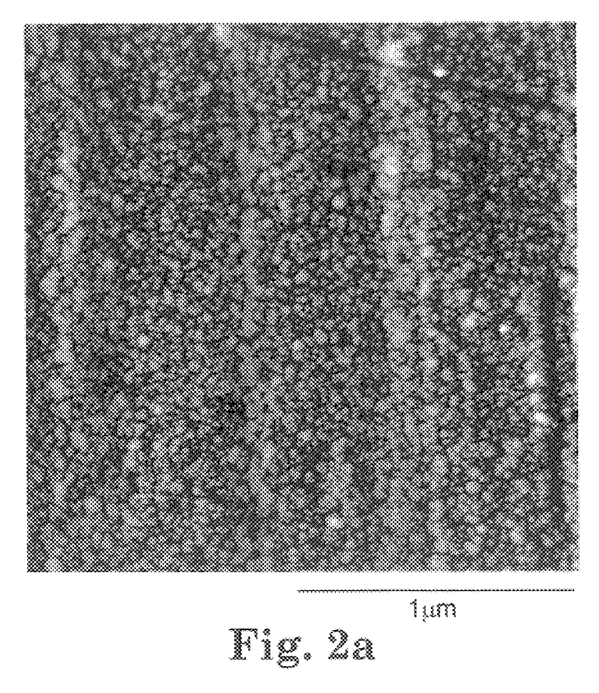
FIG. 2a is a digital image of an atomic force micrograph of the antireflective surface of the comparative, untreated antireflective glass surface.
Figure 2B:
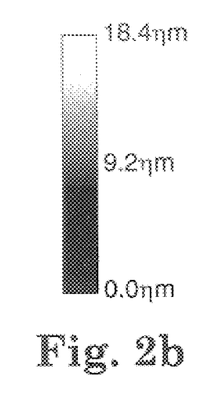

PFPE disilane/HFE-7100 solution with no acid catalyst added. Example 16A is essentially Example 16 with the exception that 0.5 mL of a solution of PFPE disilane (1 wt %), and HFE-7100 (99.0 wt %) was placed in the 10 mL view cell and the ensuing solution is sprayed lightly onto antireflective glass (product designated CDAR/CDAR, available from Viratec Thin Films, Faribault, Minn.). FIG. 1a is an AFM of the surface of this treated antireflective glass. FIG. 2a is an AFM of the surface of untreated antireflective glass. Comparison of these images shows that the surface microstructure of the AR glass is not changed by the application of the antisoiling coating, as the film is extremely thin relative to the size scale of the features on the surface of the AR film stack. Despite this reduced coating thickness, the film still exhibits outstanding antisoiling properties as measured by the ink test (as described in WO 99/37720).

Example 17

Acid catalyzed PFPE disilane/HFE-7100 solution. 1.0 mL of a solution of PFPE disilane (1 wt %), and HFE-7100 (99.0 wt %) was placed in the 10 mL view cell and pressurized with carbon dioxide. The cell was heated to 40° C. and the hazy mixture was spray-coated onto glass slides. The spray-coated glass was post-treated with acid catalyst as described in the general experimental. Durability of the coatings was measured by repeating the contact angle measurements after buffing and after 1000 scrub cycles, according to the abrasion test described above. Results of water and hexadecane contact angle measurements are listed in Table 5.

Example 18

Acid catalyzed neat PFPE disilane. One drop of PFPE disilane was placed in the 10 mL view cell and pressurized with carbon dioxide. The cell was heated to 40° C. and the hazy mixture was spray-coated onto glass slides. The spray-coated glass was post-treated with acid catalyst as described in the general experimental. Durability of the coatings was measured by repeating the contact angle measurements after buffing and after 1000 scrub cycles, according to the abrasion test described above. Results of water and hexadecane contact angle measurements are listed in Table 5.

TABLE 5

| | Contact Angle (°) | | |
|---|---|---|---|
| Example | Initial Water/hexadecane | After Buff Water/Hexadecane | After 1000 scrubs Water/Hexadecane |
| C1 | 70/45 | 72/42 | 74/42 |
| C2 | 46/62 | 33/43 | 34/28 |
| C3 | 51/43 | 43/65 | 46/43 |
| C4 | 53/65 | 37/64 | 33/23 |
| C5 | Too low | 33/64 | 30/22 |
| 16 | 80/61 | 94/61 | 75/49 |
| 17 | 91/58 | 102/64 | 98/46 |
| 18 | 107/68 | 102/63 | 97/64 |

The data in Table 5 demonstrate that formulations incorporating comparative compositions (Table 5; C1, C2, C3, C4 C5) consistently exhibit lower water contact angles than the acid catalysed compositions of this invention (Table 5; Examples 17 and 18). Additionally, the composition of this invention with no acid catalyst added (Table 5; Example 16) exhibited superior water contact angles to the comparative compositions.

Example 19

Reduced concentration of PFPE Disilane in HFE 7100/ HFE 7500 (0.05%).

Antireflective glass coupons (TDAR/TDAR, available from Viratec Thin Films) were degraded by exposure to ultrasound for several minutes in a bath consisting of a 1:1 (v/v) mixture of ethanol and chloroform, dried under nitrogen, then given a final cleaning by exposure in a UV/ozone chamber for 3 minutes. A concentrate consisting of 0.5 g of PFPE disilane and 0.05 g of glacial acetic acid in 50 g of HFE 7100 and 50 g of HFE 7500 was prepared. A 1.0 mL aliquot of the concentrate was placed in the 10 mL view cell and subsequently filled with liquid $CO_2$. This mixture was sprayed onto the antireflective glass coupons and the samples were heated in a 120° C. oven for 5 minutes. Upon cooling, static contact angles (water/hexadecane) were determined. The samples were then lightly buffed to remove any excess coating material using a 3M High Performance Wipe wetted with HFE 7100 and contact angles were again determined, with the results shown in Table 6. The coated substrates were also written on using a Sharpie™ permanent marker. It was observed that the ink beaded up and was very easy to remove both before and after buffing.

Example 20

Reduced concentration of PFPE Disilane in HFE 7100/ HFE 7500 (0.033%).

Antireflective glass coupons (TDAR/TDAR, available from Viratec Thin Films) were degraded by exposure to ultrasound for several minutes in a bath consisting of a 1:1 (v/v) mixture of ethanol and chloroform, dried under nitrogen, then given a final cleaning by exposure in a UV/ozone chamber for 3 minutes. A concentrate consisting of 0.5 g of PFPE-disilane and 0.05 g of glacial acetic acid in 50 g of HFE 7100 and 100 g of HFE 7500 was prepared. A 1.0 mL aliquot of the concentrate was placed in the 10 mL view cell and subsequently filled with liquid CO2. This mixture was sprayed onto the antireflective glass coupons and the samples were heated in a 120° C. oven for 5 minutes. Upon cooling, static contact angles (water/hexadecane) were determined. The samples were then lightly buffed to remove any excess coating material using a 3M High Performance Wipe wetted with HFE 7100 and contact angles were again determined, with the results shown in Table 6. The coated substrates were also written on using a Sharpie™ permanent marker. It was observed that the writing beaded up and was very easy to remove both before and after buffing.

TABLE 6

| Example | Substrate | Pre-Buffing Water Contact Angle/ Hexadecane Contact Angle | Post-Buffing Water contact angle/ Hexadecane contact angle |
|---|---|---|---|
| Control | Untreated TDAR | <30/0 | |
| 19 | TDAR/TDAR | 107.8 (0.1)/67.3 (0.2) | 108.2 (0.4)/68.0 (0.9) |
| 20 | CDAR/CDAR | 110.4 (1.8)/68.4 (1.5) | 104.0 (1.7)/67.4 (0.4) |

What is claimed is:
1. Composition for treating a substrate comprising a homogeneous mixture of:
(a) at least one fluorinated silane of the formula:

wherein $R_f^1$ represents a monovalent or divalent perfluorinated group,
Q represents an organic divalent linking group, wherein the sum of the number of carbon atoms and the number of heteroatoms in Q is at least 3;

$R^1$ represents a $C_1$–$C_4$ alkyl group,

Y represents a hydrolysable group;

x is 0 or 1 and y is 1 or 2;

(b) compressed fluid carbon dioxide.

2. The composition of claim 1, further comprising an organic or inorganic acid.

3. Composition according to claim 2 wherein said organic acid is a carboxylic acid.

4. Composition according to claim 2 wherein said organic acid is a fluorinated organic acid.

5. Composition according to claim 1 wherein said fluorinated silane has a solubility in said carbon dioxide of at least 0.01% by weight at ambient temperature.

6. Composition according to claim 1 wherein $R_f^1$ comprises repeating units selected from the group consisting of —($C_nF_{2n}$)—, —($C_nF_{2n}O$)—, —(CF(Z))—, —(CF(Z)O)—, —(CF(Z)$C_nF_{2n}O$)—, —($C_nF_{2n}$CF(Z)O)—, and —($CF_2$CF(Z)O)—, and combinations thereof, wherein n is at least 1 and wherein Z is a fluorine atom, a perfluoroalkyl group, an oxygen-substituted perfluoroalkyl group, a perfluoroalkoxy group, or an oxygen-substituted perfluoroalkoxy group.

7. Composition according to claim 1, wherein said fluorinated silane is selected from the group consisting of $C_7F_{15}CH_2OCH_2CH_2CH_2SiCl_3$; $C_7F_{15}CH_2OCH_2CH_2CH_2Si(CH_3)Cl_2$; $C_7F_{15}CH_2OCH_2CH_2CH_2SiCl(OCH_3)_2$; $C_7F_{15}CH_2OCH_2CH_2CH_2SiCl_2(OC_2H_5)$; $C_8F_{17}SO_2N(Et)CH_2CH_2CH_2SiCl_3$; $C_8F_{17}SO_2N(Me)CH_2CH_2CH_2Si(CH_3)Cl_2$; $C_4F_9SO_2N(Me)CH_2CH_2CH_2SiCl_3$; $C_4F_9SO_2N(Me)CH_2OCH_2CH_2Si(OCH_3)_3$; $C_3F_7CH_2OCH_2CH_2CH_2SiCl(OCH_3)_2$; and $C_7F_{15}CH_2OCH_2CH_2CH_2Si(OAc)_3$.

8. Composition according to claim 1, wherein said fluorinated silane is selected from the group consisting of $XCF_2O(CF_2O)_m(C_2F_4O)_pCF_2X$, $C_3F_7O(CF(CF_3)CF_2O)_pCF(CF_3)X$, $XCF_2O(C_2F_4O)_pCF_2X$, $XCF(CF_3)(OCF_2CF(CF_3))_mO(C_nF_{2n})O(CF(CF_3)CF_2O)_pCF(CF_3)X$, $CF_3O(C_2F_4O)_pCF_2X$, and $X(CF_2)_3O(C_4F_8O)_p(CF_2)_3X$, wherein X is -Q-SiY$_{3-x}$R$_x^1$, $C_nF_{2n+1}$, $C_nF_{2n+1}O$— or X'$C_nF_{2n}O$—, wherein X' is H, Cl, or Br, n is 2 to 4, m is 1 to 50, p is 1 to 50, with the proviso that at least one X group per molecule is -Q-SiY$_{3-x}$R$_x^1$, wherein Q represents an organic divalent linking group, $R^1$ represents a $C_1$–$C_4$ alkyl group, Y represents a hydrolysable group; x is 0 or 1 and y is 1 or 2.

9. Composition of claim 1 further comprising water.

10. Composition of claim 1 further comprising an organic solvent.

11. Composition according to claim 10 wherein said organic solvent further comprises a fluorinated solvent.

12. The composition of claim 1, further comprising a non-fluorinated silane.

13. Composition of claim 1 wherein $R_f^1$=—CF(CF$_3$)(OCF$_2$CF(CF$_3$))$_m$O($C_nF_{2n}$)O(CF(CF$_3$)CF$_2$O)$_p$CF(CF$_3$)—;

m+p=4 to 12; n=4.

14. The composition of claim 1 wherein said fluorinated silane is of the formula (CH$_3$O)$_3$Si(CH$_2$)$_3$NHC(O)OCH$_2$CF(CF$_3$) (OCF$_2$CF(CF$_3$))$_m$O($C_nF_{2n}$)O(CF(CF$_3$)CF$_2$O)$_p$CF(CF$_3$)—CH$_2$OC(O)NH(CH$_2$)$_3$Si(OCH$_3$)$_3$, where n=2 to 4, m=1 to 10, p=1 to 10, and m+p is less than or equal to 20.

15. The composition of claim 1 wherein fluorinated silane is of the formula:

$$R_f^1\text{-[-Q-SiY}_{3-x}R^1{}_x]_y \quad (I)$$

wherein $R_f^1$ is -CF(CF$_3$)(OCF$_2$CF(CF$_3$))$_m$O($C_nF_{2n}$)O(CF(CF$_3$)CF$_2$O)$_p$CF(CF$_3$)-, wherein m and p are numbers from 1 to 20;

m+p≤20; n=2 to 4,

Q represents an organic divalent linking group, wherein the sum of the number of carbon atoms and the number of heteroatoms in Q is at least 3;

$R^1$ represents a $C_1$–$C_4$ alkyl group,

Y represents hydrolysable group; and x is 0 or 1, and y is 2.

16. The composition of claim 1 wherein $r_f^{1=-CF}{}_2O(CF_2O)_m(CF_2CF_2O)_pCF_2$-; and m+p=16 to 24.

* * * * *

UNITED STATES PATENT AND TRADEMARK OFFICE
CERTIFICATE OF CORRECTION

PATENT NO. : 6,656,258 B2
DATED : December 2, 2003
INVENTOR(S) : Elsbernd, Cheryl L. S.

It is certified that error appears in the above-identified patent and that said Letters Patent is hereby corrected as shown below:

Column 21,
Line 38, delete "$C_nF_{2n+1}$," and insert in place thereof -- $C_nF_{2n+1}-$, --

Column 22,
Line 24, delete "$R_f^1-[-Q-SiY_{3-x}R^1_X]_y$" and insert in place thereof
-- $R_f^1-[-Q-SiY_{3-x}R^1_X]_y$ --
Line 26, delete "$-CF(CF_3)_{(OCF2}CF(CF_3))_m$" and insert in place thereof
-- $-CF(CF_3)(OCF2CF(CF_3))m$ --
Line 34, after "Y represents" insert in place thereof -- a --
Line 37, delete "$r_f^{1=-CF}2O$" and insert in place thereof -- $R_f^{1=}-CF2O$ --

Signed and Sealed this

Fourteenth Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 6,656,258 B2
DATED : December 2, 2003
INVENTOR(S) : Elsbernd, Cheryl L. S.

It is certified that error appears in the above-identified patent and that said Letters Patent is hereby corrected as shown below:

Title page,
Item [56], References Cited, OTHER PUBLICATIONS, please delete the last 2 duplicate entries,
"W.C. Bunyard, F.E. Henon, S.N. Burns, R.W. Linton, R.G. Carbonell, J.M. DeSimone, *"Synthesis of Novel Perfluoropolyethers for Carbon Dioxide-Based Coatings Technologies"*, University of North Carolina, Dept. of Chemistry, pp. 1-10, no date provided." and
J. Lewis, J.N. Argyropoulos, K.A. Nielson, *"Supercritical Carbon Dioxide Spray Systems"*, Metal Fininshing, (Apr., 1997).".

Column 5,
Line 11, delete "$(C_kH_{2k}K)$" and insert in place thereof -- $C_kH_{2k}$ --.
Line 15, delete "$–CH_2OC(O(N(R)$" and insert in place thereof -- $–CH_2OC(O)N(R)$ --.
Line 17, delete "$(C_kH2k)$" and insert in place thereof -- $C_kH_{2k}$ --.

Column 6,
Line 7, after "$C_nF_{2n+}1$" and insert in place thereof -- $C_nF_{2n+1}$ --.

Column 11,
Line 22, delete "$HOC(O)CF_2(CF_2O)^{TM}$" and insert in place thereof -- $HOC(O)CF_2(CF_2O)_n$ --.

Signed and Sealed this

Thirtieth Day of August, 2005

JON W. DUDAS
*Director of the United States Patent and Trademark Office*